(12) United States Patent
Matsumoto et al.

(10) Patent No.: US 11,559,195 B2
(45) Date of Patent: Jan. 24, 2023

(54) RIGID ENDOSCOPE COVER AND ENDOSCOPE UNIT

(71) Applicants: TRYTEC Co. Ltd., Oita (JP); NAGASAKI UNIVERSITY, Nagasaki (JP)

(72) Inventors: Keitaro Matsumoto, Nagasaki (JP); Katsunori Takagi, Nagasaki (JP); Takeshi Nagayasu, Nagasaki (JP); Hiroshi Takezaki, Oita (JP)

(73) Assignees: TRYTEC Co., Ltd., Oita (JP); NAGASAKI UNIVERSITY, Nagasaki (JP)

( * ) Notice: Subject to any disclaimer, the term of this patent is extended or adjusted under 35 U.S.C. 154(b) by 143 days.

(21) Appl. No.: 17/050,943

(22) PCT Filed: Jun. 12, 2019

(86) PCT No.: PCT/JP2019/023285
§ 371 (c)(1),
(2) Date: Oct. 27, 2020

(87) PCT Pub. No.: WO2019/240170
PCT Pub. Date: Dec. 19, 2019

(65) Prior Publication Data
US 2021/0228069 A1   Jul. 29, 2021

(30) Foreign Application Priority Data
Jun. 15, 2018   (JP) .............................. JP2018-114533

(51) Int. Cl.
*A61B 1/12*   (2006.01)
*A61B 1/00*   (2006.01)

(52) U.S. Cl.
CPC .......... *A61B 1/126* (2013.01); *A61B 1/00135* (2013.01)

(58) Field of Classification Search
CPC ..... A61B 1/126; A61B 1/00135; A61B 1/015; A61B 1/3132; A61B 1/00071; A61B 1/005; A61B 1/127; A61B 90/70
See application file for complete search history.

(56) References Cited

U.S. PATENT DOCUMENTS

| 5,575,756 A | 11/1996 | Karasawa et al. |
| 2011/0087072 A1* | 4/2011 | James .................... A61B 1/126 600/157 |

(Continued)

FOREIGN PATENT DOCUMENTS

| JP | 06189893 A | 7/1994 |
| JP | 2539980 B2 | 10/1996 |

(Continued)

OTHER PUBLICATIONS

Espacenet English Translation of JP3186191U (Year: 2013).*

(Continued)

*Primary Examiner* — Ryan N Henderson
*Assistant Examiner* — Megan Elizabeth Monahan
(74) *Attorney, Agent, or Firm* — Renner, Kenner, Greive, Bobak, Taylor & Weber

(57) ABSTRACT

A cover 20 for covering a circumferential portion of an outer circumferential surface of a rigid endoscope 10 having an observation window portion 14 provided at a tip thereof includes a flexible outer cover member 22 covering the circumferential portion of the circumferential surface of the rigid endoscope 10 and a tubular member 26, provided inside the outer cover member 22, through which a cleaning fluid to be supplied from a base end of the rigid endoscope 10 to the observation window portion 14 of the rigid endoscope 10 flows inside, and the outer cover member 22 is attached to the outer circumference surface of the rigid endoscope 10 by flexing the outer cover member 22.

13 Claims, 4 Drawing Sheets

(56) References Cited

U.S. PATENT DOCUMENTS

2014/0296629 A1 10/2014 Chang
2014/0296848 A1* 10/2014 Chang .................. A61M 25/00
                                                    606/41
2015/0257633 A1  9/2015 Hassidov et al.

FOREIGN PATENT DOCUMENTS

| JP | 10043131 A | 2/1998 | |
|---|---|---|---|
| JP | 11128160 A | 5/1999 | |
| JP | 2012187138 A | 10/2012 | |
| JP | 3186191 U * | 9/2013 | |
| JP | 3186191 U | 9/2013 | |
| JP | 5368511 B2 | 12/2013 | |
| JP | 5373732 B2 | 12/2013 | |
| JP | 2016537079 A | 12/2016 | |
| JP | 2017534318 A | 11/2017 | |
| JP | 6242560 A | 12/2017 | |
| WO | WO-2013040175 A2 * | 3/2013 | ......... A61B 1/00101 |

OTHER PUBLICATIONS

International Search Report for International application No. PCT/JP2019/023285 dated Sep. 3, 2019.
Written Opinion of the International Searching Authority for International application No. PCT/JP2019/023285 dated Sep. 3, 2019.
Extended European Search Report for PCT/JP2019023285 dated Feb. 10, 2022.
Office Action dated Jan. 11, 2022 for Japanese Patent Application No. 2018-114533 with English translation.
Office Action dated Jun. 16, 2022 for Japanese Patent Application No. 2018-1114533 with English translation.

* cited by examiner

RIGID ENDOSCOPE COVER AND ENDOSCOPE UNIT

TECHNICAL FIELD

The present invention relates to a cover for covering an outer circumference surface of a rigid endoscope with an observation window portion provided at a tip to protect an objective lens for taking an image of an affected area, and an endoscope unit including the rigid endoscope and the cover.

BACKGROUND ART

In recent years, in the medical field, endoscopes (soft endoscopes) represented by a stomach camera have been used in examination and surgery of the stomach. In many cases, a thoracoscope is used in surgery performed with the chest opened, and a laparoscope is used in surgery performed with the abdomen opened (hereinafter, referred to as laparoscopic surgery). Laparoscopic surgery is rapidly spreading due to its low invasiveness and good aesthetic outcome, and is mainly used for gastric cancer and colon cancer surgery, and the proportion of laparoscopic surgery to total surgery is increasing year by year. Meanwhile, the above-described thoracoscope and laparoscope, etc., are called rigid endoscopes. At a tip of a rigid endoscope, an objective lens for taking an image of an affected area is provided, and an observation window portion is also provided to protect the objective lens.

During surgery using a rigid endoscope such as the above-described thoracoscope or laparoscope, the observation window portion provided at the tip of the rigid endoscope often becomes cloudy or becomes dirty with blood, fat, etc. For this reason, there is a problem that the surgery has to be temporarily interrupted for washing or cleaning the observation window portion and thus the surgery efficiency is significantly reduced. To explain in more detail, information required for the surgery using the rigid endoscope is only image (visual) information obtained by the rigid endoscope, and cloudiness of the observation window portion or dirt on the observation window portion due to bipod, fat, etc., during the surgery hinders the surgery from being safely performed. For this reason, it is necessary to take out the rigid endoscope from the body and wash the rigid endoscope during the surgery, but the time required for this leads to an increase in the surgery time, which may cause a heavy burden on the patient or an unexpected complication.

In order to solve such a problem, there is known a technology that, as a cleaning device (specifically, a long tube), that supplies a cleaning solution such as saline or the like and air for blowing the cleaning solution to the observation window portion of the rigid endoscope inside the patient's body, is attached to the outer circumference surface of the rigid endoscope, the observation window portion is cleaned without removing the rigid endoscope from the body. For example, JPH05207962A, JPH06289388A and JP4960076B disclose technology that a supply passage of the cleaning solution and/or air is provided inside the rigid endoscope. However, as rigid endoscopes are inserted into the patient's body and must be thoroughly sterilized before use, there is a problem that the rigid endoscope, which has the internal supply passage of the cleaning solution and/or air, is complicated and does not allow for adequate sterilization of the internal supply channel, in addition, there is a problem that a manufacturing cost of the rigid endoscope would be high if the supply passage of the cleaning solution and/or air is provided inside the rigid endoscope.

JP5368511B, JPH06189893A, JP5373732B and JPH10043131 disclose a technology for cleaning the observation window portion by placing a cleaning sheath over the rigid endoscope and flowing cleaning solution and/or air into a flow channel formed between an inner surface of the cleaning sheath and an outer circumference surface of the rigid endoscope. However, in the endoscope unit disclosed in JP5388511B, JPH06189893A, JP5373732B and JPH10043131 A, an entire gap formed between the inner surface of the cleaning sheath and the outer circumference surface of the rigid endoscope is filled with the cleaning solution, which causes a slow response when the supply of the cleaning solution is stopped, in addition, there was a problem with the residual dripping of the cleaning solution remaining between the inner surface of the cleaning sheath and the outer circumference surface of the rigid endoscope.

JP2539980B discloses a technology that a cleaning tube through which the cleaning solution or the like flows is glued to the outer circumference surface of the rigid endoscope by an adhesive. Also, Japanese Utility Model Registration No. 3188101 (JP3186191U) discloses a technology for attaching a long tube through which the cleaning solution or the like flows inside to the outer circumference surface of the rigid endoscope by a tube mounting portion. However, in the endoscope unit disclosed in JP2539980B the cleaning tube is simply glued to the outer circumferential surface, of the rigid endoscope by the adhesive. Then, an adhesive surface between the cleaning tube and the outer circumferential surface of the rigid endoscope is not strong enough to allow the cleaning tube to easily come off from the outer circumferential surface of the rigid endoscope, and the tube may remain in the patient's body. The endoscope unit disclosed in JP3188191U also could cause the long tube to detach from the rigid endoscope inside the patient's body when the rigid endoscope is inserted info the patient's body, in this case, the dislodged tube could cause damage to the patient's body, in addition, the long tube had to be cleaned each time before a rigid endoscope operation was performed, which was time-consuming. Further, there was a problem that the insertion of the rigid endoscope disclosed in JP3188191U into the patient's body is obstructed by a step at the tube mounting portion.

JP6242560B discloses a cover in which an inner cover portion is provided on an inner surface of an outer coyer member, which compartmentalizes a flow passage of the cleaning solution or the like supplied to the observation window portion of the rigid endoscope. However, the cover disclosed in JP 6242560B has a problem that leakage of the cleaning solution or the like may occur from a gap between the outer cover member and the inner cover portion when the pressure of the cleaning solution or the like flowing through the flow passage compartmentalized by the inner cover part is increased.

SUMMARY OF THE INVENTION

The present invention has been made taking into account the problems of the technology disclosed in the various conventional documents described above and it is an object of the present invention to provide a rigid endoscope cover and an endoscope unit that can be easily attached to and detached from an outer circumference surface of the rigid endoscope and that ensures that a tubular member through which a cleaning fluid flows inside is not dislodged from the rigid endoscope and that prevents leakage of the cleaning solution or the like.

DESCRIPTION OF THE PREFERRED EMBODIMENTS

Figure 1:
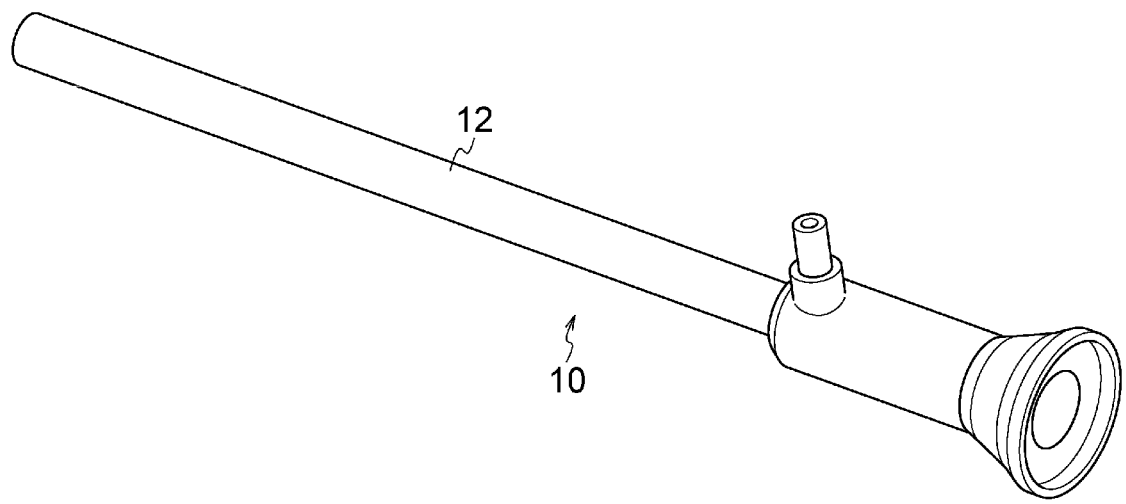
FIG. 1 is a perspective view schematically illustrating a structure of a rigid endoscope in an endoscope unit according to an embodiment of the present invention.
Figure 2:
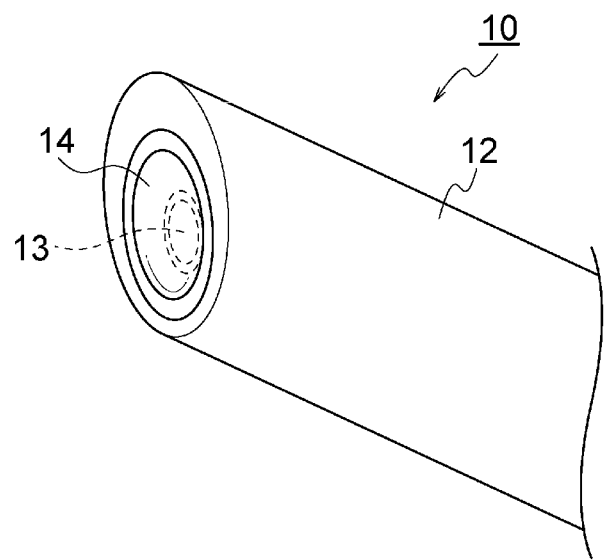
FIG. 2 is an enlarged view showing the structure of a tip of the rigid endoscope shown in FIG. 1.
Figure 3:
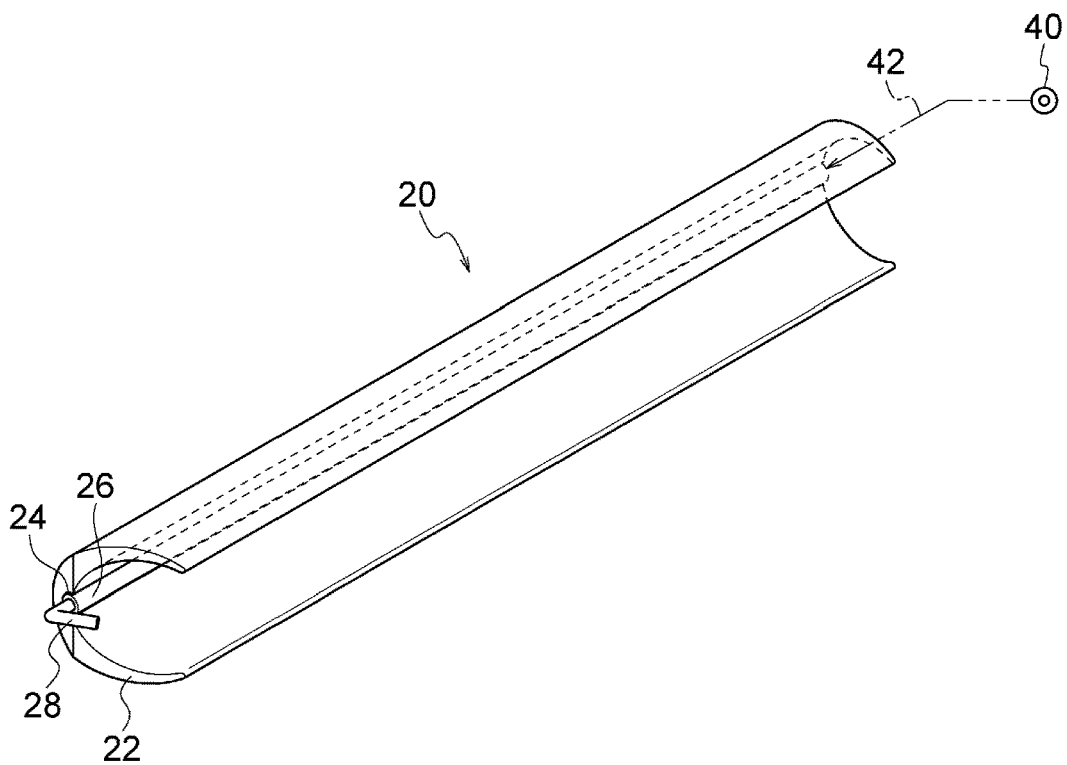
FIG. 3 is a perspective view showing a structure of a cover in the endoscope, unit according to the embodiment of the present invention.
Figure 4:
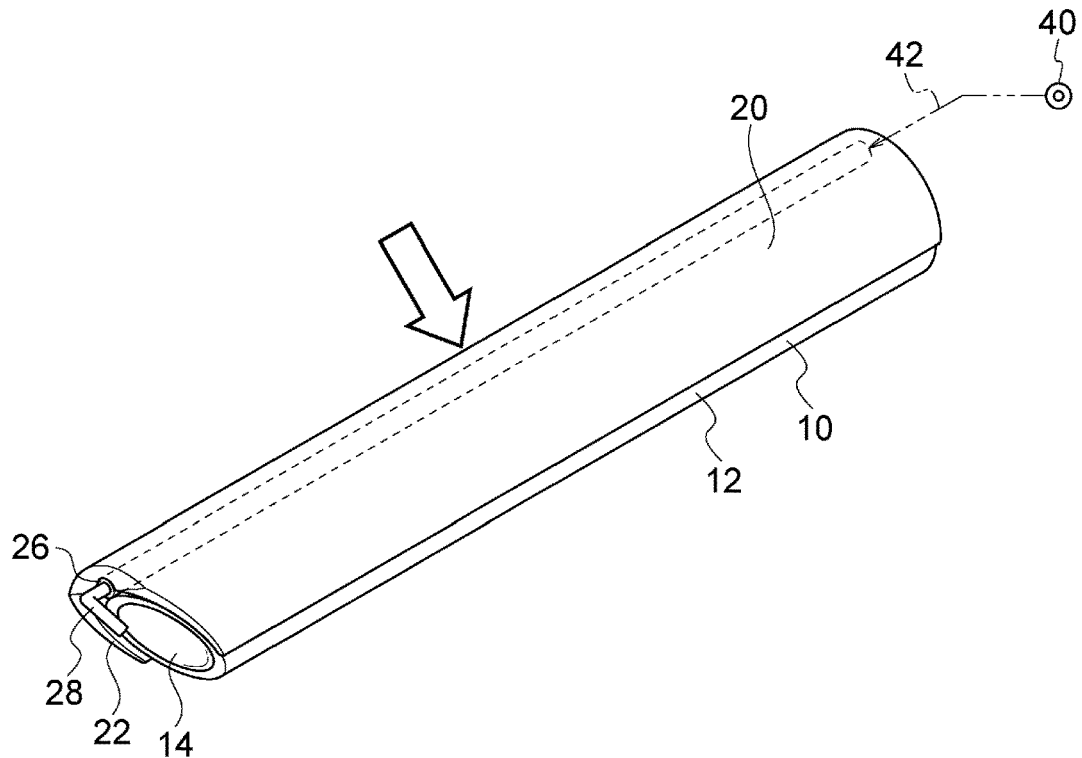
FIG. 4 is a perspective view showing a state of the rigid endoscope shown in FIG. 1 covered by the cover shown in FIG. 3 in the embodiment of the present invention.
Figure 5:
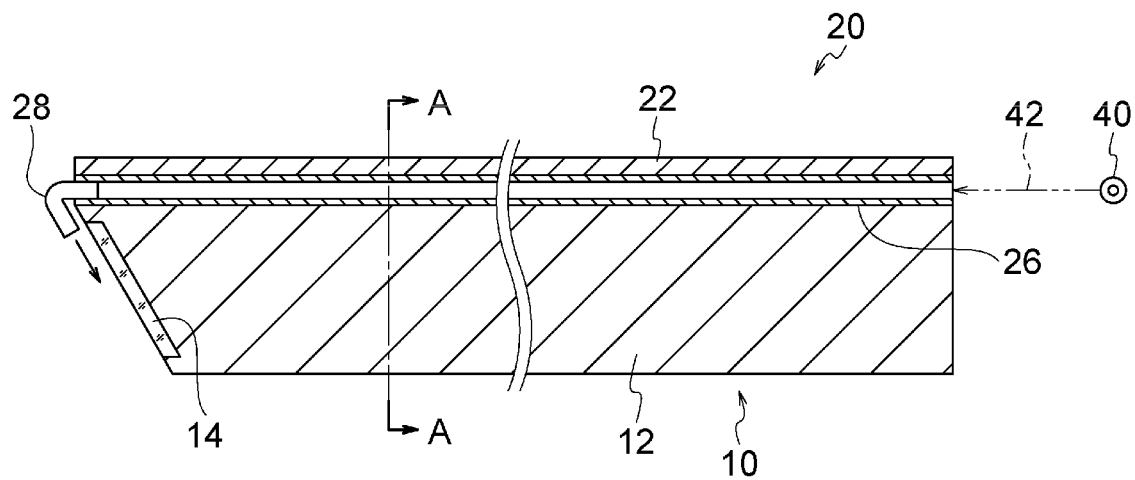
FIG. 5 is a cross-sectional view of the endoscope unit shown in FIG. 4.
Figure 6:
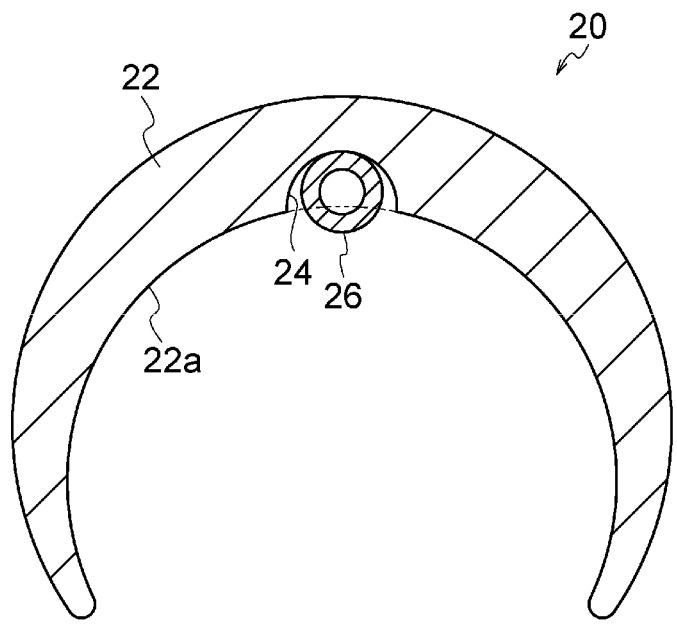
FIG. 6 is a cross-sectional view of the cover of the endoscope unit shown in FIG. 5, in view of an A-A arrow.
Figure 7:
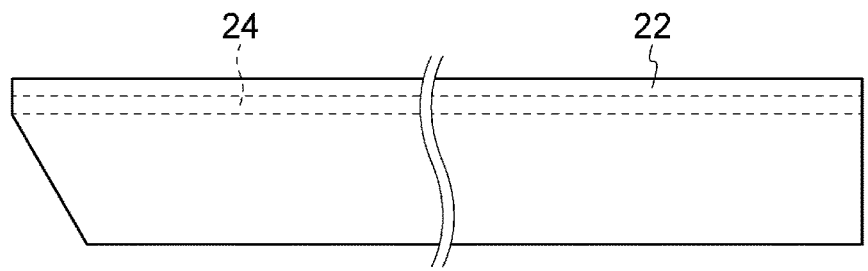
FIG. 7 is a side view of the structure of the cover shown in FIG. 6 when viewed from a left and right direction.
Figure 8:
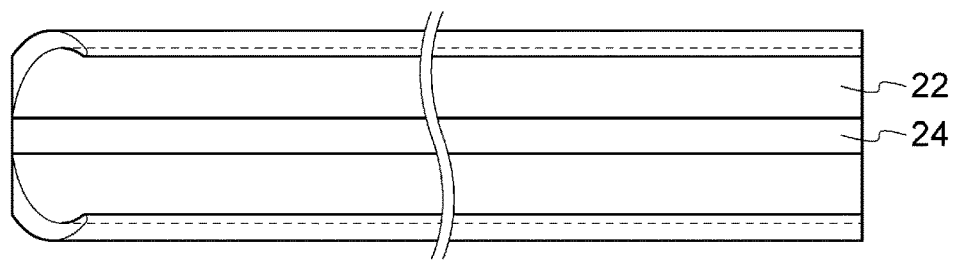
FIG. 8 is a lower view of the cover shown in FIG. 8 when viewed from below.

Hereinafter, an embodiment of the present invention will be described with reference to the drawings. FIGS. 1 to 8 illustrate an endoscope unit according to the present embodiment. Among these figures, FIG. 1 is a perspective view schematically illustrating a structure of a rigid endoscope in the endoscope unit according to the present embodiment, and FIG. 2 is an enlarged view showing the structure of a tip of the rigid endoscope shown in FIG. 1. FIG. 3 is a perspective view showing a structure of a cover in the endoscope unit according to the present embodiment. FIG. 4 is a perspective view showing a state of the rigid endoscope shown in FIG. 1 covered by the cover shown in FIG. 3 in the embodiment of the present invention, FIG. 5 is a cross-sectional view of the endoscope unit shown in FIG. 4, and FIG. 6 is a cross-sectional view of the cover of the endoscope unit shown in FIG. 5, in view of an A-A arrow, FIG. 7 is a side view of the structure of the cover shown in FIG. 6 when viewed from a left and right direction, and FIG. 8 is a lower view of the cover-shown in FIG. 6 when viewed from below.

The endoscope unit according to the present embodiment comprises the rigid endoscope 10 shown in FIGS. 1 and 2 and the cover 20 shown in FIG. 3 and the like. Specifically, as shown in FIG. 4, the endoscope unit according to the present embodiment has the cover 20 attached to an outer circumference surface of the rigid endoscope 10.

First, the rigid endoscope 10 according to the present embodiment will be described with reference to FIGS. 1 and 2. As shown in FIGS. 1 and 2, the rigid endoscope 10 has an elongated substantially cylindrical body portion 12, and an objective len 13 for taking an image of an affected area and an observation window portion 14 such as a glass plate that protects the objective tens 13 are provided at a tip of the body portion 12. As shown in FIG. 5, a tip surface (i.e., a surface on a left side in FIG. 5) of the elongated substantially cylindrical body portion 12 is inclined with respect to a surface (i.e., a surface extending, in a vertical direction in FIG. 5) perpendicular to a longitudinal direction of the body portion 12. The observation window port ion 14 is provided on the inclined tip surface. For this reason, the observation window portion 14 is inclined with respect to the plane perpendicular to the longitudinal direction of the elongated substantially cylindrical body portion 12. It is noted that the rigid endoscope according to the present embodiment is not limited to such a configuration. Another example of the rigid endoscope according to the present embodiment may be used such that an observation member extends along the plane perpendicular to the longitudinal direction of the elongated substantially cylindrical body portion.

Next, FIG. 3 to FIG. 8 will be used to describe the cover 20 for covering a circumferential portion of the outer circumference surface of the rigid endoscope 10 in a circumferential direction of the rigid endoscope 10 according to the present embodiment. As shown in FIG. 3 and the like, the cover 20 according to the present embodiment has an outer cover member 22 and the tubular member 26. The outer cover member 22 covers the circumferential portion of the outer circumference surface of the rigid endoscope 10. The tubular member 26 is provided inside the outer cover member 22. A cleaning fluid such as the cleaning fluid, air or the like to be supplied from a base end of the rigid endoscope 10 to the observation window portion 14 of the rigid endoscope 10 flows inside the tubular member 26. As shown in FIG. 4, 5 or the like, the outer cover member 22 extends over a substantially entire length of the rigid endoscope 10. As shown in FIG. 3 or the like, the outer cover member 22 has a substantially C-shaped shape when viewed along the longitudinal direction of the outer cover member 22, and the rigid endoscope 10 is fitted into the space between the C-shaped portion. The outer cover member 22 is composed of a plastic such as a soft plastic, and the outer cover member 22 is flexible. The outer cover member 22 is then flexed so that the outer cover member 22 is attached to the outer circumference surface of the rigid endoscope 10. In more detail, when attaching the cover 20 to the rigid endoscope 10, the outer circumference surface of the rigid endoscope 10 is pressed to the gap of the C-shaped portion of the outer cover member 22, and then the outer cover member 22 is pushed toward the outer circumference surface of the rigid endoscope 10. The direction in which the outer cover member 22 is pushed against the rigid endoscope 10 is indicated by an arrow in FIG. 4. This deforms the outer cover member 22 to widen the gap between the C-shaped portion of the outer cover member 22 so that the cover 20 is attached, to the rigid endoscope 10.

As shown in FIG. 3, 6 or the like, a groove 24 is provided on an inner surface 22a of the outer cover member 22 opposite the outer circumference surface of the rigid endoscope 10. The tubular member 26 is fitted into this groove 24. As shown in FIG. 7, 8 or the like, the groove 24 extend in a straight line over the entire length of the outer cover member 22. The tubular member 28 comprises an elongated cylindrical tube or the like made of rubber such as silicone rubber (especially medical silicone rubber) or Teflon rubber. Such tubular member 26 also extends over the entire length of the outer cover member 22. As shown in FIG. 5, a fluid supply source 40 is connected to a base end portion of the tubular member 26 via a fluid supply passage 42. The clean fluid such as the cleaning solution, air or the like is supplied from the fluid supply source 40 to the inside of the tubular member 26 via the fluid supply passage 42.

In the present embodiment, the tubular member 26 is fixed to the inside of the outer cover member 22 (specifically, the inside of the groove 24) by an adhesive. Instant adhesives or medical adhesives (for example, art adhesive conforming to ISO 10993 such as LOCTITE (registered trademark) 4011 or the like) are preferably used as adhesives to fix the tubular member 26 to the inside of the outer cover member 22. In this process, a primer such as LOCTITE (registered trademark) SF7701 or the like may be used.

As shown in FIG. 6, it is preferable that a portion of the tubular member 26 fitted into the groove 24 is exposed to the outside of the groove 24 and then the tubular member 26 protrudes from the inner surface 22a of the outer cover member 22 towards the rigid endoscope 10. In this case, when the cover 20 is attached to the rigid endoscope 10, the tubular member 28 contacts the outer circumference surface of the rigid endoscope 10. More specifically, when the cover 20 is attached to the rigid endoscope 10, a portion of the tubular member 26 exposed outside of the groove 24 deforms elastically so that the tubular member 26 adheres to the outer circumference surface of the rigid endoscope 10. Here, simply attaching the outer cover member 22, which is made of plastic and the like, to the outer circumference surface of the rigid endoscope 10 has the following problems. Specifically, the outer cover member 22 slides against the outer circumference surface of the rigid endoscope 10 while the rigid endoscope 10 provided with the cover 20 is inserted into the patient's body for treatment, causing the outer cover member 22 to rotate in a circumferential direction of the rigid endoscope 10. As described above, the rigid endoscope 10 has the objective lens 13 at the tip of the body portion 12 for taking the image of the affected area, and this objective lens 13 is protected by the observation window portion 14, such as the glass plate, but in some cases the position of the objective lens 13 is displaced in the downward direction in FIG. 5 from the center axis of the body portion 12. If the outer cover member 22 rotates in the circumferential direction of the rigid endoscope 10 in such a case, the field of view of the objective lens 13 may be blocked by a fluid direction change portion 28, which will be described below, and the patient's internal body may not be adequately observed. In contrast, by bringing the tubular member 26 of the rubber or the like fitted into the groove 24 of the outer cover member 22 into contact with the outer circumference surface of the rigid endoscope 10, a frictional force acts between the outer circumference surface of the rigid endoscope 10 and the tubular member 26. This prevents the outer cover member 22 from rotating in the circumferential direction of the rigid endoscope 10.

The fluid direction change portion 28 is provided at the tip of the tubular member 26 to change the direction of the cleaning fluid flowing through the interior of the tubular member 26 towards the observation window portion 14 of the rigid endoscope 10. More specifically, as the fluid direction change portion 28, for example, a pipe made of metal such as a stainless steel or plastic bent in a direction from the longitudinal direction of the rigid endoscope 10 (i.e., the left and right direction in FIG. 5) to the observation window portion 14 of the rigid endoscope 10 is used. The fluid direction change portion 28 shown in FIGS. 4 and 5 is bent in a V-shape, but the fluid direction change portion 28 may be bent in an L-shape, U-shape, substantially U-shape, and the like. As shown in FIG. 5, when the fluid direction change portion 28 is bent in a V-shape, the bend angle of the fluid direction change portion 28 is approximately the same as the angle of the surface of the observation window portion 14 with respect to the longitudinal direction of the rigid endoscope 10. To explain in more detail, as described above, in the rigid endoscope 10 shown in FIG. 5 or the like, the observation window portion 14 is inclined with respect to the plane perpendicular to the longitudinal direction of the elongated substantially cylindrical body portion 12 and a point near the tubular member 26 on the apical surface of the body portion 12 is at an acute angle (e.g., approximately 60°). By setting the bend angle of the fluid direction change portion 28 to an acute angle of approximately the same magnitude as the angle of the surface of the observation window portion 14 with respect to the longitudinal direction of body portion 12 (i.e., approximately 60°), the cleaning fluid whose flow direction is changed by the fluid direction change portion 28 can be reliably supplied to the observation window portion 14. If another example of the rigid endoscope according to the present embodiment is used in which the observation member extends along the plane perpendicular to the longitudinal direction of the elongated substantially cylindrical body portion, the bend angle of the fluid direction change portion 28 will be approximately 90°. The bend angle of the fluid direction change portion 28 does not necessarily have to be the substantially same as the angle of the surface of the observation window portion 14 with respect to the longitudinal direction of the rigid endoscope 10. As long as the surface of the observation window portion 14 is cleaned by the cleaning fluid discharged from the tip of the fluid direction change portion 28 hitting the surface of the observation window portion 14, the bend angle of the fluid direction change portion 28 can be set to any size.

Next, the use of the endoscope unit comprising such configuration will be described. First, when performing the surgery in which the endoscope unit is inserted into the patient's body, the cover 20 shown in FIG. 3 is attached to the outer circumference surface of the rigid endoscope 10 shown in FIGS. 1 and 2. Specifically, the gap of the C-shaped portion of the outer cover member 22 is pressed against the outer circumference surface of the rigid endoscope 10, and the outer cover member 22 is pushed against the outer circumference surface of the rigid endoscope 10. This deforms the outer cover member 22 so that the gap of the C-shaped portion of the outer cover member 22 is widened, then the cover 20 is attached to the rigid endoscope 10. In this way, the endoscope unit is formed with the cover 20 attached to the outer circumference surface of the rigid endoscope 10, as shown in FIG. 4. The surgery is then performed by inserting the endoscope unit into the patient's body, as shown in FIG. 4.

If the observation window portion 14 of the rigid endoscope 10 becomes contaminated or clouded by blood, fat, etc. during surgery, the observation window portion 14 is cleaned while the endoscope unit is inserted into the patient's body. In more detail, the cleaning solution is supplied from the fluid supply source 40 to the interior of the tubular member 26 via the fluid supply passage 42. This causes the cleaning solution to flow in the left direction in FIG. 5 inside the tubular member 26. The direction of the cleaning solution flowing in the left direction in FIG. 5 is then changed by the fluid direction change portion 28 toward the observation window portion 14. That is, the direction of the cleaning solution flowing in the left direction in FIG. 5 inside the tubular member 26 is changed from the left direction in FIG. 5 to the lower right direction in FIG. 5 by the fluid direction change portion 28. This allows the observation window portion 14 to be cleaned with the cleaning solution. Then, air is supplied from the fluid supply source 40 to the interior of the tubular member 26 through the fluid supply passage 42. This allows the cleaning solution attached to the observation window portion 14 to be blown away by air.

According to the cover 20 of the present embodiment comprising the above configuration and the endoscope unit comprising such cover 20 and rigid endoscope 10, the tubular member 26 provided inside the outer cover member 22 allows the cleaning fluid to be supplied from the base end of the rigid endoscope 10 to the observation window portion 14 of the rigid endoscope 10 so that the observation window portion 14 can be cleaned in the patient's body.

In addition, in the present embodiment, the outer cover member 22 flexes so that the outer cover member 22 is attached to the outer circumference surface of the rigid endoscope 10. This allows easy attachment and removal of the cover 20 with respect to the rigid endoscope 10. For this reason, the cover 20 can be disposable for each surgery. Traditionally, the cover was fixed to the rigid endoscope so that it could not be removed for each operation. However, in this case, the cover must be thoroughly sterilized before the rigid endoscope is used, but sterilizing the cover while it is attached to the rigid endoscope is cumbersome for the user. On the other hand, if the cover 20 is disposable such as the rigid endoscope 10 of the present embodiment, it is more convenient for the user to simply remove the cover 20 from the rigid endoscope 10 and dispose the cover 20 after surgery.

Further, according to the cover 20 of the present embodiment, the cleaning fluid is supplied to the observation window portion 14 of the rigid endoscope 10 from the base end of the rigid endoscope 10 by using the tubular member 26. This prevents leakage of the cleaning solution or the like from the cover 20 at midway point in the longitudinal direction of the rigid endoscope 10.

Also, in the present embodiment, the groove 24 is provided on the inner surface 22a of the outer cover member 22 and the tubular member 26 is fitted inside the groove 24. This allows the rigid endoscope 10 (i.e., the endoscope unit) with the cover 20 attached to has a relatively small outer diameter. Thus, it improves surgical efficiency and prevents damage to the patient's body. In addition, when the groove 24 is provided on the inner surface 22a of outer cover member 22 and the tubular member 26 is fitted inside this groove 24, as in the case of the cover 20 of the present embodiment, manufacturing costs can be reduced compared to manufacturing a cleaning sheath with internal penetration of the supply passage of the cleaning solution, air or the like.

In the present embodiment, by attaching the fluid direction change portion 28 made of a metal pipe or the like to the tip of the tubular member 26, the direction of the cleaning solution or the like flowing through the tubular member 26 can be reliably changed. Therefore, the cleaning fluid can be reliably supplied to the observation window portion 14.

The rigid endoscope cover and endoscope unit of the present invention are not limited to the aforementioned manner and can be modified in various ways.

For example, the tubular member through which the cleaning fluid to be supplied from the base end of the rigid endoscope to the observation window portion of the rigid endoscope flows inside may not be limited to a cylindrical one. An elliptical tubular member with an internal space may be used as the tubular member.

In the above description, the groove is provided on the inner surface of the outer cover member and the tubular member is glued to the inside of the groove by the adhesive. However, the present invention is not limited to this manner. As another example, a groove with a shape such that the tubular member does not come off when the tubular member is fitted, even if the tubular member is not glued in place by the adhesive. Specifically, the cross-sectional shape of the groove may be, for example, a substantially circular shape with notch in a portion of the groove. In this case, the tubular member can be fitted into the groove provided on the inner surface of the outer cover member without using the adhesive.

In the explanation above, the cover is described in a manner such that the tubular member and fluid direction change portion are separate. However, in a cover related to a variation, a tubular member and a fluid direction change portion may be used as a single entity. In this case, the material of the fluid direction change portion and the material of the tubular member may be the same.

Figure 9:
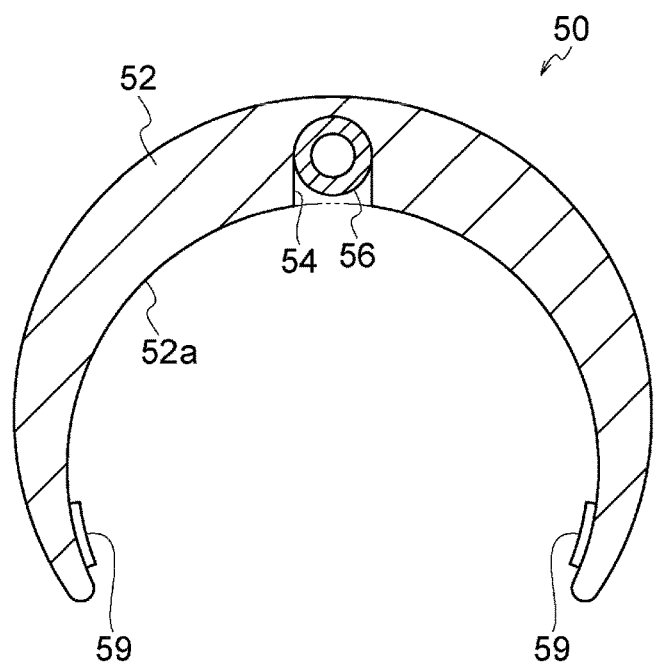
FIG. 9 is a cross-sectional view of a cover related to a variation.

In the above description, the portion of the tubular member fitted into the groove is exposed to the outside of the groove, and the tubular member protrudes from the inner surface of the outer cover member toward the rigid endoscope side. However, the present invention is not limited to this manner. Another type of cover may be used as a variation in which a tubular member is completely within the groove and this tubular member does not protrude outwardly from the inner surface of the outer cover member. FIG. 9 will be used to describe such a variant of the cover.

The cover 50 shown in FIG. 9 has an outer cover member 52 covering the circumferential portion of the outer circumference surface of the rigid endoscope and a tubular member 56 provided inside the outer cover member 52 and through which the cleaning fluid such as the cleaning solution or the like to be supplied from the base end of the rigid endoscope to the observation window portion of the rigid endoscope flows inside. The outer cover member 52 has a substantially C-shape when viewed along the longitudinal direction of the outer cover member 52, and the rigid endoscope is fitted into the space of the C-shaped portion. A groove 54 is provided on an inner surface 52a of the outer cover member 52 opposite the outer circumference surface of the rigid endoscope, and the tubular member 56 is fitted into the groove 54. The tubular member 56 is completely inside groove 54, and the tubular member 56 does not protrude outward from the inner surface 52a of the outer cover member 52.

In the cover 50 shown in FIG. 9, two friction members 59 are provided on the inner surface 52a of the outer cover member 52 to exert frictional forces between the outer circumference surface of the rigid endoscope and each friction member 59. More specifically, the friction members 59 are provided on the inner surface 52a in the vicinity of both ends of the outer cover member 52, respectively. Each friction member 59 comprises, for example, a rubber such as silicone rubber (in particular, medical silicone rubber) or Teflon rubber. A pair of friction members 59 are provided on the inner surface 52a of the outer cover member 52, thereby exerting the frictional forces between the outer circumference surface of the rigid endoscope and the outer cover member 52 through each friction member 59. This prevents the outer cover member 52 from rotating in the circumferential direction of the rigid endoscope. In more detail, in the cover 50 shown in FIG. 9, as the tubular member 56 is completely within the groove 54, without each friction member 59, no frictional force would act between the tubular member 58 and the outer circumference surface of the rigid endoscope when the cover 50 is attached to the outer circumference surface of the rigid endoscope. This may cause the outer cover member 52 to slide against the outer circumference surface of the rigid endoscope, causing the outer cover member 52 to rotate in the circumferential direction of the rigid endoscope. In contrast, when each friction member 59 is provided, the friction forces act between the outer circumference surface of the rigid endoscope and the outer cover member 52 through each friction member 59. This prevents the outer cover member 52 from rotating in the circumferential direction of the rigid endoscope.

In yet another variant of the cover, in a case where the portion of the tubular member fitted into the groove formed on the inner surface of the outer cover member is exposed to the outside of the groove and the tubular member protrudes from the inner surface of the outer cover member towards the rigid endoscope side, as shown in FIG. 6, each friction member 59 as shown in FIG. 9 may be additionally provided on the inner surface of the outer cover member. In this case, the outer cover member will be more reliably prevented from rotating in the circumferential direction of the rigid endoscope.

The invention claimed is:

1. A cover for covering a circumferential portion of an outer circumferential surface of a rigid endoscope having an observation window portion provided at a tip thereof, the cover comprising: a flexible outer cover member covering the circumferential portion of the outer circumferential surface of the rigid endoscope; and a tubular member, provided inside the flexible outer cover member, through which a cleaning fluid to be supplied from a base end of the rigid endoscope to the observation window portion of the rigid endoscope flows inside, wherein the flexible outer cover member is attached to the outer circumference surface of the rigid endoscope by flexing the flexible outer cover member, wherein a portion of the tubular member fitted into a groove, formed within an inner surface of the outer cover member, is exposed to an outside of the groove and then the tubular member protrudes from the inner surface of the flexible outer cover member, the inner surface of the flexible outer cover being where the outer circumferential surface of the rigid endoscope contacts when the rigid endoscope is attached to the flexible outer cover, towards the rigid endoscope such that the portion of the tubular member exposed outside of the groove deforms elastically so that the tubular member adheres to the outer circumference surface of the rigid endoscope and a frictional force acts between the outer circumference surface of the rigid endoscope and the tubular member.

2. The cover according to claim 1, wherein the flexible outer cover member extends over substantially an entire length of the rigid endoscope.

3. The cover according to claim 1, wherein a cross section of the flexible outer cover member along a plane perpendicular to a longitudinal direction of the rigid endoscope is substantially C-shaped.

4. The cover according to claim 1, wherein a material of the flexible outer cover member is a plastic material.

5. The cover according to claim 1, wherein a material of the tubular member is a rubber material.

6. The cover according to claim 1, wherein the groove is provided on the inner surface of the flexible outer cover member opposite the outer circumference surface of the rigid endoscope, and the tubular member is fitted into the groove.

7. The cover according to claim 1, wherein the tubular member is fixed to the inside of the flexible outer cover member by an adhesive.

8. The cover according to claim 1, wherein a fluid direction changer is provided at the a tip of the tubular member to change the direction of the cleaning fluid flowing through an interior of the tubular member to a direction toward the observation window portion of the rigid endoscope.

9. The cover according to claim 8, wherein the fluid direction changer is a metal or plastic pipe bent in a direction from a longitudinal direction of the rigid endoscope to the observation window portion of the rigid endoscope.

10. The cover according to claim 8, wherein the fluid direction changer is bent in a V-shape, L-shape, U-shape, or substantially U-shape.

11. The cover according to claim 8, wherein a bend angle of the fluid direction changer is approximately the same as an angle of a surface of the observation window portion with respect to a longitudinal direction of the rigid endoscope.

12. The cover according to claim 1, wherein a friction member is provided on the inner surface of the flexible outer cover member opposite the outer circumference surface of the rigid endoscope to exert a friction force between the outer circumference surface of the rigid endoscope and the friction member.

13. An endoscope unit comprising: a rigid endoscope having an observation window portion provided at a tip thereof; and a cover configured to cover a circumferential portion of an outer circumferential surface of the rigid endoscope, wherein the cover has a flexible outercover member covering the circumferential portion of the outer circumferential surface of the rigid endoscope and a tubular member, provided inside the flexible outercover member, through which a cleaningfluid to be supplied from a base end of the rigid endoscope to the observation window portion of the rigid endoscope flows inside, and the flexible outer cover member is attached to the outer circumference surface of the rigid endoscope by flexing the flexible outercover member, wherein a portion of the tubular member fitted into a groove, formed within an inner surface of the outer cover member, is exposed to an outside of the groove and then the tubular member protrudes from the inner surface of the flexible outer cover member, the inner surface of the flexible outer cover being where the outer circumference surface of the rigid endoscope contacts when the rigid endoscope is attached to the flexible outercover, towards the rigid endoscope such that the portion of the tubular member exposed outside of the groove deforms elastically so that the tubular member adheres to the outer circumference surface of the rigid endoscope and a frictional force acts between the outer circumference surface of the rigid endoscope and the tubular member.

* * * * *